United States Patent
Knopff

(10) Patent No.: US 10,807,941 B2
(45) Date of Patent: Oct. 20, 2020

(54) PROCESS FOR THE PREPARATION OF POLYSANTOL-TYPE COMPOUNDS

(71) Applicant: Firmenich SA, Satigny (CH)

(72) Inventor: Oliver Knopff, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/301,756

(22) PCT Filed: Jun. 1, 2017

(86) PCT No.: PCT/EP2017/063351
§ 371 (c)(1),
(2) Date: Nov. 15, 2018

(87) PCT Pub. No.: WO2017/207707
PCT Pub. Date: Dec. 7, 2017

(65) Prior Publication Data
US 2019/0292127 A1    Sep. 26, 2019

(30) Foreign Application Priority Data
Jun. 3, 2016  (EP) ..................................... 16172962

(51) Int. Cl.
| | |
|---|---|
| *C07C 69/145* | (2006.01) |
| *C07C 69/24* | (2006.01) |
| *C07C 69/14* | (2006.01) |
| *C07C 67/08* | (2006.01) |
| *C07C 49/172* | (2006.01) |
| *C07C 49/21* | (2006.01) |
| *C07C 45/72* | (2006.01) |
| *C07C 45/65* | (2006.01) |
| *C11B 9/00* | (2006.01) |

(52) U.S. Cl.
CPC ............ *C07C 69/145* (2013.01); *C07C 45/65* (2013.01); *C07C 45/72* (2013.01); *C07C 49/172* (2013.01); *C07C 49/21* (2013.01); *C07C 67/08* (2013.01); *C07C 69/14* (2013.01); *C07C 69/24* (2013.01); *C11B 9/0019* (2013.01); *C11B 9/0026* (2013.01); *C07C 2601/10* (2017.05); *C07C 2601/14* (2017.05); *C07C 2601/16* (2017.05)

(58) Field of Classification Search
CPC ....... C07C 67/08; C07C 49/21; C07C 49/172; C07C 45/72; C07C 45/65; C07C 69/145; C07C 69/14; C07C 69/24; C11B 9/0026
See application file for complete search history.

(56) References Cited

PUBLICATIONS

Castro et al, Tetrahedron Letters, Synthesis of Polysantol® and related sandalwood-type odorants using magnesium a-bromoketone enolates, 2004, 45, pp. 2619-2622. (Year: 2004).*
Benkeser et al, Journal of the American Chemical Society, Factors Influencing the Direction of Elimination in Ester Pyrolyses, 1959, 81 (20), pp. 5374-5379. (Year: 1959).*
International Search Report and Written Opinion for international application No. PCT/EP2017/063351 dated Jul. 6, 2017.
Benkeser et al., "Factors Influencing the Direction of Elimination in Ester Pyrolyses", Journal of the American Chem. Soc., (1959), vol. 81 (20), pp. 5374-5379.
Castro et al., "Enantiospecific synthesis, separation and olfactory evaluation of all diastereomers of a homologue of the sandalwood odorant Polysantol®", Tetrahedron, (2005), vol. 61(47), pp. 11192-11203.
Castro et al., "Synthesis of Polysantol® and related sandalwood-type odorants using magnesium α-bromoketone enolates", Tetrahedron Lett., (2004), vol. 45 (12), pp. 2619-2622.
Fehr et al., "161. General Synthesis of Ketones from Carboxylic Esters and Carboxamides by Use of Mixed Organolithium-Magnesium Reagents . . . ", Helvetica Chimica Acta, (1987), vol. 70 (7), pp. 1745-1752.

* cited by examiner

*Primary Examiner* — Paul A Zucker
(74) *Attorney, Agent, or Firm* — Armstrong Teasdale LLP

(57) ABSTRACT

The present invention relates to the field of organic synthesis and more specifically it concerns a novel compound of formula (I). The invention additionally relates to a process for preparing a compound of formula (III) using the compound of formula (I) as an intermediate, wherein the process involves elimination of the R3(X)nC(=O)O functional group of the compound of formula (I).

13 Claims, No Drawings

PROCESS FOR THE PREPARATION OF POLYSANTOL-TYPE COMPOUNDS

RELATED APPLICATIONS

This application is a national stage application under 35 U.S.C. § 371 filing of International Patent Application PCT/EP2017/063351, filed Jun. 1, 2017, which claims the benefit of EP Patent Application no 16172962.9, filed Jun. 3, 2016.

TECHNICAL FIELD

The present invention relates to the field of organic synthesis and more specifically it concerns a novel compound of formula (I) which could be used as a novel intermediate in the process for the preparation of compound of formula (III).

BACKGROUND

Sandalwood ingredients, such as Polysantol® (trademark from Firmenich SA), are much appreciated perfumery ingredients. In general, they are synthesized by aldol condensation starting from an aldehyde such as α-campholenic aldehyde. In particular, Polysantol® is obtained by an aldol condensation between α-campholenic aldehyde and ethyl methyl ketone following by a methylation and reduction. This synthetic route presents several drawbacks; i.e. the regioselectivity of the first step of this synthesis is challenging, side product are formed during the methylation step which requires the use of methylchloride.

A lot of efforts have been made for improving each step of this route or even to pass through different intermediates. In *Tetrahedron Lett.* 2004, 45 (12), 2619-2622, the aldol reaction has been replaced by a Grignard reaction between α-campholenic aldehyde and 3-bromo-3-methylbutan-2-one to provide the alcohol 4-hydroxy-3,3-dimethyl-5-(2,2,3-trimethylcyclopent-3-en-1-yl)pentan-2-one. However the industrial scale up of this step could be tedious and the difficulty to eliminate the obtained alcohol encountered by the authors has raised prejudice toward this route.

Therefore, there is still a need to develop an efficient route to synthesize Polysantol® while limiting side product formation, favoring the desired regioisomer and improving the productivity. The present invention provides a novel intermediate toward the synthesis of Polysantol® allowing to develop a new synthetic process more efficient and straightforward than what was previously known.

DESCRIPTION OF THE INVENTION

We have now found that the derivatives of formula (III) can be produced in an advantageous manner using compound of formula (I) as an intermediate.

Therefore, a first object of the present invention is a compound of formula (I)

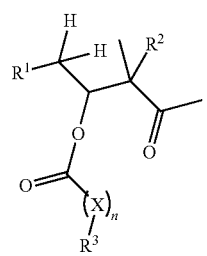

(I)

in the form of any one of its stereoisomers or a mixture thereof, and wherein $R^1$ represents a $C_{5-11}$ branched alkyl or a $C_{6-11}$ alicyclic group optionally comprised an ether functional group, $R^2$ represents a hydrogen atom or a methyl group, n is 0 or 1; X represents a $NR^3$ group, or oxygen atom; and $R^3$ represents, independently from each other, a hydrogen atom or a $C_{1-6}$ alkyl group or an aryl group.

For the sake of clarity, by the expression "alicyclic group", or the similar, it is meant the normal meaning understood by the person skilled in the art, i.e. a cyclic saturated or unsaturated alkyl group optionally substituted by aliphatic groups.

For the sake of clarity, by the expression "any one of its stereoisomers", or the similar, it is meant the normal meaning understood by a person skilled in the art, i.e. that the invention compound can be a pure enantiomer (if chiral) or diastereomer.

According to any one of the above embodiments of the invention, said compounds of formula (I) are $C_{14}$-$C_{23}$ compounds.

According to any one of the above embodiments of the inventions, $R^1$ represents a $C_{5-6}$ cycloalkyl or cycloalkenyl group substituted by 1 to 3 $C_{1-3}$ alkyl or alkenyl group optionally comprising an ether group or a $C_{5-8}$ branched alkyl group. Preferably, $R^1$ represents a $C_{5-6}$ cycloalkyl or cycloalkenyl group substituted by 1 to 3 methyl group and optionally substituted by a methylene group or a $C_{5-6}$ branched alkyl group. Even more preferably, $R^1$ represents a $C_5$ cycloalkyl or cycloalkenyl group substituted by 3 methyl group.

For the sake of clarity, by the term "methylene group", it is meant the normal meaning in the art; i.e. a $CH_2$ group linked by a double bond to the cycloalkyl or cycloalkenyl group.

According to any one of the above embodiments of the inventions, $R^2$ represents a methyl group.

According to any one of the above embodiments of the inventions, $R^3$ represents a $C_{1-3}$ alkyl group or an aryl group. Preferably, $R^3$ represents a methyl, an ethyl, a propyl or an isopropyl group, even more preferably, $R^3$ represents a methyl or an ethyl group. Even more preferably, $R^3$ represents a methyl group.

According to any one of the above embodiments, n is 0, and so the $R(X)_nC(=O)O$ group is an ester.

According to any one of the above embodiments of the inventions, the compound of the invention is of formula (II)

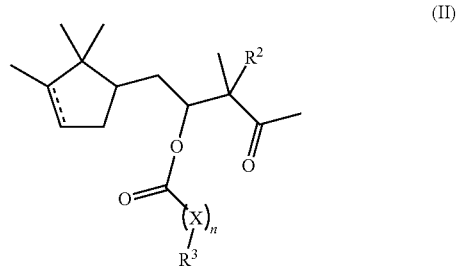

(II)

in the form of any one of its stereoisomers or a mixture thereof, wherein n, X, $R^2$ and $R^3$ have the same meaning as above, and the dotted line represents a carbon-carbon single or double bond.

For the sake of clarity, by the expression "wherein the dotted line represents a carbon-carbon single or double bond", or the similar, it is meant the normal meaning understood by a person skilled in the art, i.e. that the whole bonding (solid and dotted lines) between the carbon atoms connected by said dotted line is a carbon-carbon single or double bond.

According to any one of the above embodiments of the inventions, the compound of the invention is formula (IIa)

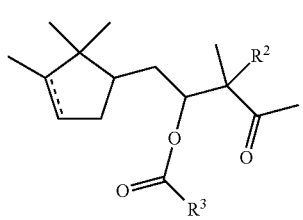

(IIa)

in the form of any one of its stereoisomers or a mixture thereof, wherein $R^2$ and $R^3$ have the same meaning as above, and the dotted line represents a carbon-carbon single or double bond.

According to any one of the above embodiments of the inventions, the compound of formula (I) are the acetate or propionate of 3,3-dimethyl-4-oxo-1-(2,2,3-trimethylcyclopent-3-en-1-yl)pentan-2-yl, 1-(2,2-dimethyl-3-methylenecyclohexyl)-3,3-dimethyl-4-oxopentan-2-yl, 3,3-dimethyl-4-oxo-1-(2,2,3-trimethylcyclohex-3-en-1-yl)pentan-2-yl or 3-methyl-4-oxo-1-(2,2,3-trimethylcyclopent-3-en-1-yl)pentan-2-yl. Preferably, the compound of formula (I) are the acetate or propionate of 3,3-dimethyl-4-oxo-1-(2,2,3-trimethylcyclopent-3-en-1-yl)pentan-2-yl, 1-(2,2-dimethyl-3-methylenecyclohexyl)-3,3-dimethyl-4-oxopentan-2-yl or 3,3-dimethyl-4-oxo-1-(2,2,3-trimethylcyclohex-3-en-1-yl)pentan-2-yl. Even more preferably, the compound of formula (I) is 3,3-dimethyl-4-oxo-1-(2,2,3-trimethylcyclopent-3-en-1-yl)pentan-2-yl acetate.

The compound of formula (I) may be used as an intermediate toward the synthesis of compound of formula (III). So another object of the present invention is a process for the preparation of a compound of formula (III)

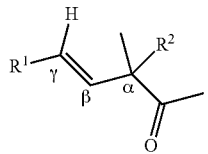

(III)

in the form of any one of its stereoisomers or a mixture thereof, wherein $R^1$ and $R^2$ have the same meaning as above; comprising the step of elimination of $R(X)_nC(=O)O$ functional group of compound of formula (I) as defined above.

According to any one of the above embodiments, the step of elimination of the $R(X)_nC(=O)O$ functional group leads to the generation of a double bond. Said elimination step is a pyrolysis. Said pyrolysis is performed at a temperature between 400° C. and 600° C., preferably between 450° C. and 550° C. Preferably, this elimination is performed on a purified compound of formula (I). This pyrolysis, unexpectedly, give compound of formula (III) with a yield superior to 80%, even more, superior to 90% despite the fact that the pyrolysis on hindered substrates with a gem dimethyl are known to be less productive (*Helv. Chim. Acta* 1987, 70 (7), 1745-1752).

According to any one of the above embodiments, when $R^2$ represents a hydrogen atom, the compound of formula (III) is a mixture comprising a β-γ unsaturated ketone and α-β unsaturated ketone.

According to any one of the above embodiments, the compound of formula (III) is of formula (IV)

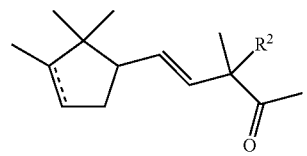

(IV)

wherein $R^2$ and the dotted line have the same meaning as above. In another words, the process of present invention is a process for the preparation of a compound of formula (IV)

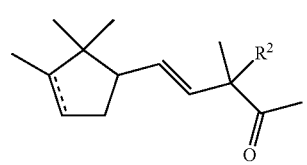

(IV)

wherein $R^2$ and the dotted line have the same meaning as above.

According to any one of the above embodiments, the process of present invention is a process for the preparation of 3,3-dimethyl-5-(2,2,3-trimethylcyclopent-3-en-1-yl)pent-4-en-2-one, 3-methyl-5-(2,2,3-trimethylcyclopent-3-en-1-yl)pent-4-en-2-one, 5-(2,2-dimethyl-3-methylenecyclohexyl)-3,3-dimethylpent-4-en-2-one or 3,3-dimethyl-5-(2,2,3-trimethylcyclohex-3-en-1-yl)pent-4-en-2-one. Preferably, the process of present invention is a process for the preparation of 3,3-dimethyl-5-(2,2,3-trimethylcyclopent-3-en-1-yl)pent-4-en-2-one, 5-(2,2-dimethyl-3-methylenecyclohexyl)-3,3-dimethylpent-4-en-2-one or 3,3-dimethyl-5-(2,2,3-trimethylcyclohex-3-en-1-yl)pent-4-en-2-one. Even more preferably, the process of present invention is a process for the preparation of 3,3-dimethyl-5-(2,2,3-trimethylcyclopent-3-en-1-yl)pent-4-en-2-one. In another word, the compound of formula (III) may be selected from the group of 3,3-dimethyl-5-(2,2,3-trimethylcyclopent-3-en-1-yl)pent-4-en-2-one, 3-methyl-5-(2,2,3-trimethylcyclopent-3-en-1-yl)pent-4-en-2-one, 5-(2,2-dimethyl-3-methylenecyclohexyl)-3,3-dimethylpent-4-en-2-one and 3,3-dimethyl-5-(2,2,3-trimethylcyclohex-3-en-1-yl)pent-4-en-2-one. Preferably, the compound of formula (III) may be selected from the group of 3,3-dimethyl-5-(2,2,3-trimethylcyclopent-3-en-1-yl)pent-4-en-2-one, 5-(2,2-dimethyl-3-methylenecyclohexyl)-3,3-dimethylpent-4-en-2-one and 3,3-dimethyl-5-(2,2,3-trimethylcyclohex-3-en-1-yl)pent-4-en-2-one. Even more preferably, the compound of formula (III) may be 3,3-dimethyl-5-(2,2,3-trimethylcyclopent-3-en-1-yl)pent-4-en-2-one.

According to any above embodiment, the process of the present invention further comprises the step of preparing compound of formula (I) from compound of formula

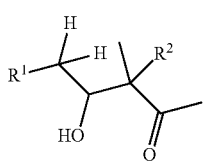

in the form of any one of its stereoisomers or a mixture thereof, wherein $R^1$ and $R^2$ have the same meaning as above. In another words, the compound of formula (I) can be obtained from compound of formula (V).

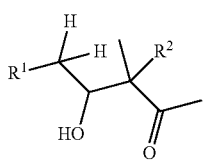

in the form of any one of its stereoisomers or a mixture thereof, wherein $R^1$ and $R^2$ have the same meaning as above.

According to any one of the above embodiments, the compound of formula (V) can be a compound of formula (VI)

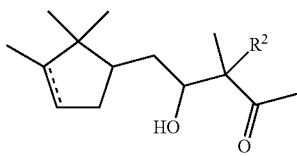

wherein $R^2$ and the dotted line have the same meaning as above. In another word, the compound of formula (I) can be obtained from compound of formula (VI)

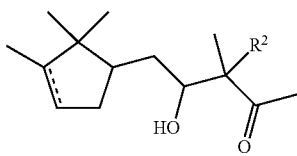

wherein $R^2$ and the dotted line have the same meaning as above.

According to any one of the above embodiments, the compound of formula (I) can be obtained from 4-hydroxy-3,3-dimethyl-5-(2,2,3-trimethylcyclopent-3-en-1-yl)pentan-2-one, 4-hydroxy-3-methyl-5-(2,2,3-trimethylcyclopent-3-en-1-yl)pentan-2-one, 5-(2,2-dimethyl-3-methylenecyclohexyl)-4-hydroxy-3,3-dimethylpentan-2-one or 4-hydroxy-3,3-dimethyl-5-(2,2,3-trimethylcyclohex-3-en-1-yl)pentan-2-one. Preferably, the compound of formula (I) can be obtained from 4-hydroxy-3,3-dimethyl-5-(2,2,3-trimethylcyclopent-3-en-1-yl)pentan-2-one, 5-(2,2-dimethyl-3-methylenecyclohexyl)-4-hydroxy-3,3-dimethyl-pentan-2-one or 4-hydroxy-3,3-dimethyl-5-(2,2,3-trimethylcyclohex-3-en-1-yl)pentan-2-one. Even more preferably, the compound of formula (I) can be obtained from 4-hydroxy-3,3-dimethyl-5-(2,2,3-trimethylcyclopent-3-en-1-yl)pentan-2-one. In another word, the compound of formula (V) may be selected from the group of 4-hydroxy-3,3-dimethyl-5-(2,2,3-trimethylcyclopent-3-en-1-yl)pentan-2-one, 4-hydroxy-3-methyl-5-(2,2,3-trimethylcyclopent-3-en-1-yl)pentan-2-one, 5-(2,2-dimethyl-3-methylenecyclohexyl)-4-hydroxy-3,3-dimethylpentan-2-one and 4-hydroxy-3,3-dimethyl-5-(2,2,3-trimethylcyclohex-3-en-1-yl)pentan-2-one. Preferably, the compound of formula (I) may be selected from the group of 4-hydroxy-3,3-dimethyl-5-(2,2,3-trimethylcyclopent-3-en-1-yl)pentan-2-one, 5-(2,2-dimethyl-3-methylenecyclohexyl)-4-hydroxy-3,3-dimethylpentan-2-one and 4-hydroxy-3,3-dimethyl-5-(2,2,3-trimethylcyclohex-3-en-1-yl)pentan-2-one. Even more preferably, the compound of formula (I) may be 4-hydroxy-3,3-dimethyl-5-(2,2,3-trimethylcyclopent-3-en-1-yl)pentan-2-one.

The use of compound of formula (VI) to obtain compound of formula (IV) has been reported only in *Tetrahedron Lett.* 2004, 45 (12), 2619-2622. However, the direct elimination of the alcohol is not working and the only efficient deshydratation method reported deals with the treatment of 4-hydroxy-3,3-dimethyl-5-(2,2,3-trimethylcyclopent-3-en-1-yl)pentan-2-one with methanesulfonyl chlorid before the elimination which is detrimental to the organoleptic property of Polysantol® as it leads to the presence of trace of sulfured compounds in the final product difficult to rid off. Furthermore, said method leads to the generation of chlorinated side products which is highly desirable to limit due to difficulty to treat this kind of wastes. Unexpectedly, the elimination of $R(X)_nC(=O)O$ functional group of compound of formula (I) allows avoiding this reagent and the generation of chlorinated side products and provides compound of formula (III) with higher yield than prior art.

According to any one of the above embodiments, the compound of formula (I) is obtained by treating compound of formula (V) with an appropriate source of $C(=O)XR$, e.g. $C_{2-8}$ carboxylic acid, $C_{4-16}$ carboxylic anhydride, $C_{2-8}$ acid chloride or $C_{2-8}$ isocyanate under acidic or basic condition. A detailed description of the nature and type of the base and acid is not required (and would not be exhaustive) as a person skilled in the art is well aware of the acid or base needed for this type of reaction. In other words, the process of the present invention further comprises the step of preparing compound of formula (I) by treating compound of formula (V) with an appropriate source of $C(=O)XR$, e.g. $C_{2-8}$ carboxylic acid, $C_{4-16}$ carboxylic anhydride, $C_{2-8}$ acid chloride or $C_{2-8}$ isocyanate under acidic or basic condition.

Said source of $C(=O)XR$ can be added into the reaction medium of the invention's process in a large range of concentrations. As non-limiting examples, one can cite as source of $C(=O)XR$ concentration values those ranging from about 1.1 molar equivalents to about 3 molar equivalents, relative to the amount of the compound of formula (V). Preferably, the source of $C(=O)XR$ concentration will be comprised between 1.1 molar equivalent to 1.5 molar equivalents, relative to the amount of the compound of formula (V). It goes without saying that the optimum concentration of the source of $C(=O)XR$ will depend, as the person skilled in the art knows, on the nature of the latter, on the nature of the substrate and of the temperature used during the process, as well as the desired time of reaction.

According to any one of the invention's embodiments, the invention's process to form compound of formula (I) is carried out at a temperature comprised between 25° C. and 100° C. In particular, the temperature is in the range between 75° C. and 95° C. Of course, a person skilled in the art is also able to select the preferred temperature as a function of the melting and boiling point of the starting and final products as well as the desired time of reaction or conversion.

The reaction can be carried out in the presence or absence of a solvent. When a solvent is required or used for practical reasons, then any solvent current in such reaction type can be used for the purposes of the invention. Non-limiting examples include cyclohexane, DMAP, THF, Me-THF, MTBE, DME, Et$_2$O, toluene, ethyl acetate, dichloromethane, dodecane. The choice of the solvent is a function of the nature of the C$_{2-8}$ carboxylic acid, C$_{4-16}$ carboxylic anhydride, C$_{2-8}$ acid chloride or C$_{2-8}$ isocyanate and the person skilled in the art is well able to select the solvent most convenient in each case to optimize the reaction.

According to any one of the above embodiments, the process further comprises the step of preparing the compound of formula (V) by an aldol condensation between an aldehyde of formula R$^1$CH$_2$CHO wherein R$^1$ has the same meaning as above and methyl ethyl ketone; i.e. R$^2$ is hydrogen atom or iso-propyl methyl ketone; i.e. R$^2$ is a methyl group, or by a Grignard reaction, as reported in *Tetrahedron Lett.* 2004, 45 (12), 2619-2622, between R$^1$CH$_2$CHO aldehyde and 3-bromobutan-2-one; i.e. R$^2$ is hydrogen atom or 3-bromo-3-methylbutan-2-one; i.e. R$^2$ is a methyl group. Preferably, the process further comprises the step of preparing the compound of formula (VI) as described in the prior art or by the aldol condensation between (+)-α-campholenic aldehyde and iso-propyl methyl ketone or methyl ethyl ketone. More preferably, the process further comprises the step of preparing the compound of formula (VI) by the aldol condensation between α-campholenic aldehyde and iso-propyl methyl ketone. The aldol condensation is carried out under normal condition known by the person skilled in the art, i.e. with a large molar equivalent of ethyl methyl ketone or iso-propyl methyl ketone and with a catalytic amount of a base of formula MOH wherein M represents an alkali metal, an alkaline earth metal or a quaternized ammonia in an alcoholic solution. Specific and non-limiting examples of base of formula MOH may be selected from the group consisting of potassium hydroxide, sodium hydroxide, cesium hydroxide, lithium hydroxide, barium hydroxide, calcium hydroxide, magnesium hydroxide, tetramethyl ammonium hydroxide, N,N,N-trimethylbenzenaminium hydroxide and choline hydroxide. According to any one of the invention's embodiments, the invention's process to form compound of formula (V) is carried out at a temperature comprised between −5° C. and 40° C. In particular, the temperature is in the range between −2° C. and 25° C. Of course, a person skilled in the art is also able to select the preferred temperature as a function of the melting and boiling point of the starting and final products as well as the desired time of reaction or conversion.

The reaction is carried out in the presence of a solvent. Any solvent current in such reaction type can be used for the purposes of the invention. Non-limiting examples include methanol, ethanol, water or a mixture therefore. The choice of the solvent is a function of the nature of the substrate and of the carboxylic derivative and the person skilled in the art is well able to select the solvent most convenient in each case to optimize the reaction.

In other words, the invention's process for the preparation of a compound of formula (III) comprises the step of a) an aldol condensation between methyl ethyl ketone or iso-propyl methyl ketone and an aldehyde of formula R'CH$_2$CHO wherein R$^1$ has the same meaning as above to prepare compound of formula (V);

b) treating compound of formula (V) with an appropriate source of C(=O)XR, e.g. C$_{2-8}$ carboxylic acid, C$_{4-16}$ carboxylic anhydride, C$_{2-8}$ acid chloride or C$_{2-8}$ isocyanate under acidic or basic condition to prepare compound of formula (I); and c) an elimination of R(X)$_n$C(=O)O functional group of compound of formula (I).

EXAMPLES

The invention will now be described in further details by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Preparation of (R,E)-3,3-dimethyl-5-(2,2,3-trimethylcyclopent-3-en-1-yl)pent-4-en-2-one a) 3,3-dimethyl-4-oxo-1-((R)-2,2,3-trimethylcyclopent-3-en-1-yl)pentan-2-yl acetate In a two liter flask 4-hydroxy-3,3-dimethyl-5-((R)-2,2,3-trimethylcyclopent-3-en-1-yl)pentan-2-one (267 g) and 440 mL cyclohexane was stirred at room temperature. After the addition of DMAP (6.0 g, 49 mmol) and Et$_3$N (100 g, 0.98 mol), Ac$_2$O (94 g) were added in 20 min (exothermic reaction up to 50° C.). The mixture was heated at 86° C. and further 31 g of Ac$_2$O were added. After 75 min at 86° C. the mixture was cooled down to 10° C. 581 g of a 10% aqueous solution of H$_3$PO$_4$ were added and after stirring (10 min) the organic phase (774 g) was separated and washed with 50 g of water, 25 g of water and with 25 g of a saturated aqueous NaCl solution. After washing with 50 g of a saturated aqueous NaHCO$_3$ solution the organic mixture was distilled (30° C.–104° C./0.1 mbar) to give 243.6 g (74.7% of 3,3-dimethyl-4-oxo-1-((R)-2,2,3-trimethylcyclopent-3-en-1-yl)pentan-2-yl acetate.

$^{13}$C-NMR major isomer of C: 12.6, 19.7, 19.9, 20.9, 21.3, 25.4, 26.1, 30.5, 35.2, 46.2, 46.6, 52.0, 75.3, 121.7, 148.3, 170.7, 211.3 b) (R,E)-3,3-dimethyl-5-(2,2,3-trimethylcyclopent-3-en-1-yl)pent-4-en-2-one

An isolated Inox tube with heating system (Pyrolysis Oven, 2 cm×50 cm), filled with 110 mL of glass beads (7 mm) was connected to a cooling condenser on the top of the column and to an evaporator system on the bottom. The column was heated up to 500° C. and the evaporator to 240° C. during 1 h. The whole system was set under vacuum (100 mbar). 3,3-dimethyl-4-oxo-1-((R)-2,2,3-trimethylcyclopent-3-en-1-yl)pentan-2-yl acetate (96.4 g, 73.4% GC) were added to the evaporator slowly with a syringe pump (20 g/h) and the product was evaporated at 240° C. and distilled through the column (500° C.). 85.3 g were collected with the cooling condenser in a flask. The mixture was distilled to eliminate the volatiles (AcOH) and the residue (700-20 mbar/40 to 110 C°) and 64.7 g of (R,E)-3,3-dimethyl-5-(2,2,3-trimethylcyclopent-3-en-1-yl)pent-4-en-2-one were obtained (GC 74.6%, yield of pyrolysis 87%).

$^{13}$C-NMR: 12.7, 20.5, 24.2, 25.4, 25.5, 35.3, 48.4, 50.3, 54.1, 121.4, 131.5, 135.0, 148.0, 211.6

Example 2

Preparation of (R,E)-3,3-dimethyl-5-(2,2,3-trimethylcyclopent-3-en-1-yl)pent-4-en-2-one—Comparative Example a) Dehydration Under Acidic Conditions 2 g of 4-hydroxy-3,3-dimethyl-5-((R)-2,2,3-trimethylcyclopent-3-en-1-yl)pentan-2-one were distilled in the Kugelrohr apparatous (160° C.–170° C./200-20 mbar) in the presence of 0.2 g KHSO$_4$. 1.6 g of (R)-campholenic aldehyde (80% purity) were obtained. Not any trace of the desired product (R,E)-3,3-dimethyl-5-(2,2,3-trimethylcyclopent-3-en-1-yl)pent-4-en-2-one was detected in the distillation product and in the residue.

b) Dehydration Under Acidic Conditions 2 g of 4-hydroxy-3,3-dimethyl-5-((R)-2,2,3-trimethylcyclopent-3-en-1-yl)pentan-2-one were stirred at 65° C. in 30 mL Toluene in the presence of 0.67 g (3.61 mmol) pTsOH.H$_2$O. After 60 min a complete conversion was observed and not any trace of the desired product (R,E)-3,3-dimethyl-5-(2,2,3-trimethylcyclopent-3-en-1-yl)pent-4-en-2-one was detected (only formation of (R)-campholenic aldehyde was observed).

The dehydration reaction under acidic condition does not provide the desired product. The novel intermediate, i.e. 3,3-dimethyl-4-oxo-1-((R)-2,2,3-trimethylcyclopent-3-en-1-yl)pentan-2-yl acetate, allows to obtain (R,E)-3,3-dimethyl-5-(2,2,3-trimethylcyclopent-3-en-1-yl)pent-4-en-2-one through pyrolysis reaction. Said novel intermediate is a key intermediate of the novel synthetic route toward Polysantol® preventing the methylation step and affording Polysantol® in good yield.

The invention claimed is:

1. A compound of formula (I)

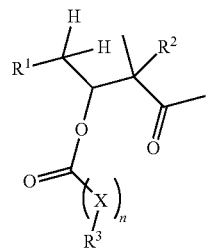

(I)

in the form of any one of its stereoisomers or a mixture thereof, and wherein R1 is a C5-11 branched alkyl or a C6-11 alicyclic group optionally comprising an ether functional group, R2 is a hydrogen atom or a methyl group, n is 0 or 1; X is a NR3 group, or oxygen atom; and R3 is, independently, a hydrogen atom or a C1-6 alkyl group or an aryl group.

2. The compound according to claim 1, characterized in that the compound is of formula

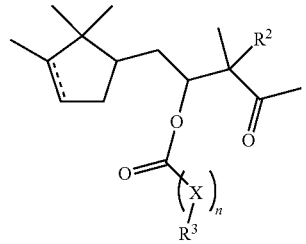

(II)

in the form of any one of its stereoisomers or a mixture thereof, wherein n, X, R2 and R3 have the same meaning as defined in claim 1, and the dotted line is a carbon-carbon single or double bond.

3. The compound according to claim 1, characterized in that the compound is of formula

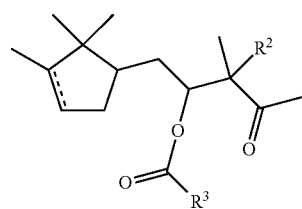

(IIa)

in the form of any one of its stereoisomers or a mixture thereof, wherein R2 and R3 have the same meaning as defined in claim 1, and the dotted line is a carbon-carbon single or double bond.

4. The compound according to claim 1, characterized in that the compound is an acetate or propionate of 3,3-dimethyl-4-oxo-1-(2,2,3-trimethylcyclopent-3-en-1-yl)pentan-2-yl, 1-(2,2-dimethyl-3-methylenecyclohexyl)-3,3-dimethyl-4-oxopentan-2-yl, 3,3-dimethyl-4-oxo-1-(2,2,3-trimethylcyclohex-3-en-1-yl)pentan-2-yl or 3-methyl-4-oxo-1-(2,2,3-trimethylcyclopent-3-en-1-yl)pentan-2-yl.

5. Process for the preparation of a compound of formula (III)

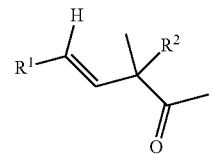

(III)

in the form of any one of its stereoisomers or a mixture thereof, wherein R1 is a C5-11 branched alkyl or a C6-11 alicyclic group optionally comprising an ether functional group, and R2 is a hydrogen atom or a methyl group;

comprising the step of eliminating an R3(X)nC(=O)O functional group from a compound of formula (I)

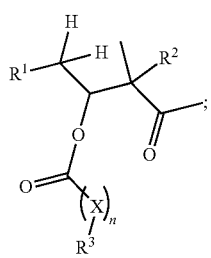

(I)

wherein R1 is a C5-11 branched alkyl or a C6-11 alicyclic group optionally comprising an ether functional group, R2 is a hydrogen atom or a methyl group, n is 0 or 1; X is a NR3 group, or oxygen atom; and R3 is, independently, a hydrogen atom or a C1-6 alkyl group or an aryl group;

wherein the elimination step is a pyrolysis.

6. The process according to claim 5, characterized in that the pyrolysis is performed at a temperature between 400 and 600° C.

7. The process according to claim 5, characterized in that the process further comprises the step of preparing compound of formula (I) from compound of formula

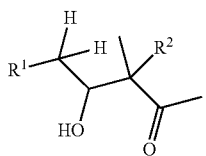

(V)

in the form of any one of its stereoisomers or a mixture thereof, wherein R1 is a C5-11 branched alkyl or a C6-11 alicyclic group optionally comprising an ether functional group, and R2 is a hydrogen atom or a methyl group.

8. The process according to claim 7, characterized in that the process further comprises the step of preparing the compound of formula (V) by an aldol condensation between iso-propyl methyl ketone or propyl methyl ketone and R1CH2CHO wherein R1 is a C5-11 branched alkyl or a C6-11 alicyclic group optionally comprising an ether functional group.

9. The process according to claim 5, characterized in that the compound of formula (III) is of formula

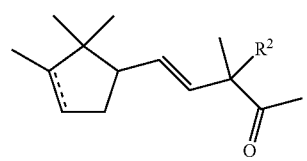

(IV)

wherein R2 is a hydrogen atom or a methyl group and the dotted line is a carbon-carbon single or double bond.

10. The process according to claim 5, characterized in that the compound of formula (III) is selected from the group consisting of 3,3-dimethyl-5-(2,2,3-trimethylcyclopent-3-en-1-yl)pent-4-en-2-one, 3-methyl-5-(2,2,3-trimethylcyclopent-3-en-1-yl)pent-4-en-2-one, 5-(2,2-dimethyl-3-methylenecyclohexyl)-3,3-dimethyl pent-4-en-2-one and 3,3-dimethyl-5-(2,2,3-trimethylcyclohex-3-en-1-yl)pent-4-en-2-one.

11. The process according to claim 7, characterized in that compound of formula (V) is of formula

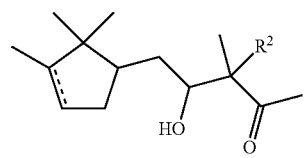

(VI)

wherein R2 is a hydrogen atom or a methyl group and the dotted line is a carbon-carbon single or double bond.

12. The process according to claim 11, characterized in that the process further comprises the step of preparing the compound of formula (VI) by the aldol condensation between α-campholenic aldehyde and iso-propyl methyl ketone or methyl ethyl ketone.

13. The process according to claim 7, characterized in that the compound of formula (V) is selected from the group consisting of 4-hydroxy-3,3-dimethyl-5-(2,2,3-trimethylcyclopent-3-en-1-yl)pentan-2-one, 4-hydroxy-3-methyl-5-(2,2,3-trimethylcyclopent-3-en-1-yl)pentan-2-one, 5-(2,2-dimethyl-3-methylenecyclohexyl)-4-hydroxy-3,3-dimethylpentan-2-one and 4-hydroxy-3,3-dimethyl-5-(2,2,3-trimethylcyclohex-3-en-1-yl)pentan-2-one.

\* \* \* \* \*